(12) United States Patent
Sturniolo et al.

(10) Patent No.: US 12,156,830 B2
(45) Date of Patent: Dec. 3, 2024

(54) INTRAUTERINE DEVICE

(71) Applicant: Upsilon Healthcare Technology, LLC, Wynnewood, PA (US)

(72) Inventors: Antonella Sturniolo, New York, NY (US); Harrison Meyer, Wynnewood, PA (US); Richard Briganti, Bala Cynwyd, PA (US); Stefanie Soichet, New York, NY (US)

(73) Assignee: Upsilon Healthcare Technology, LLC, Wynnewood, PA (US)

( * ) Notice: Subject to any disclaimer, the term of this patent is extended or adjusted under 35 U.S.C. 154(b) by 404 days.

(21) Appl. No.: 17/611,961

(22) PCT Filed: Jun. 10, 2020

(86) PCT No.: PCT/US2020/036906
§ 371 (c)(1),
(2) Date: Nov. 17, 2021

(87) PCT Pub. No.: WO2020/257014
PCT Pub. Date: Dec. 24, 2020

(65) Prior Publication Data
US 2022/0233343 A1 Jul. 28, 2022

Related U.S. Application Data

(60) Provisional application No. 62/862,056, filed on Jun. 15, 2019.

(51) Int. Cl.
*A61F 6/14* (2006.01)
*A61F 6/18* (2006.01)

(52) U.S. Cl.
CPC .............. *A61F 6/142* (2013.01); *A61F 6/14* (2013.01); *A61F 6/148* (2013.01); *A61F 6/18* (2013.01)

(58) Field of Classification Search
CPC ............ A61F 6/14; A61F 6/142; A61F 6/144; A61F 6/146; A61F 6/148; A61F 6/16
See application file for complete search history.

(56) References Cited

U.S. PATENT DOCUMENTS

| 3,353,533 A | 11/1967 | Ishihana |
| 3,507,274 A | 4/1970 | Soichet |

(Continued)

FOREIGN PATENT DOCUMENTS

| EP | 0 036 805 | 3/1981 |
| GB | 2 156 224 | 10/1985 |

OTHER PUBLICATIONS

European Search Report (Jun. 14, 2022) from European Application No. EP 20827615.

(Continued)

*Primary Examiner* — Keri J Nelson
(74) *Attorney, Agent, or Firm* — Neil D. Gershon

(57) ABSTRACT

An intrauterine device for preventing egg fertilization having a membrane, a frame having a first arm and a second arm, the first and second arms movable from a first position to a second more expanded position. The frame supports the membrane to move the membrane between a first position to a second more expanded position, wherein the first and second arms are non-planar and each arm has a proximal portion, an intermediate portion and a distal portion, The first arm has a bend at the intermediate portion so that the intermediate portion of the first arm lies in a different plane than the proximal portion of the first arm and the second arm has a bend at the intermediate portion so the intermediate portion of the second arm lies in a different plane than the proximal portion of the second arm. An elongated tail portion extends proximally of the membrane. The membrane can have a convex distal portion.

20 Claims, 20 Drawing Sheets

(56) References Cited

U.S. PATENT DOCUMENTS

| | | |
|---|---|---|
| 3,628,530 A | 12/1971 | Schwartz |
| 3,633,574 A | 1/1972 | Lerner |
| 3,645,258 A | 2/1972 | Massouras |
| 3,678,927 A | 7/1972 | Soichet |
| 3,683,906 A | 8/1972 | Robinson |
| 3,802,425 A | 4/1974 | Moulding, Jr. |
| 3,811,435 A | 5/1974 | Soichet |
| 3,899,564 A | 8/1975 | Kessler et al. |
| 3,921,954 A | 11/1975 | Monett |
| 3,923,051 A | 12/1975 | Soichet |
| 4,038,978 A | 8/1977 | Morris et al. |
| 9,089,418 B2 | 7/2015 | Tal et al. |
| 2018/0055684 A1 | 3/2018 | Lad et al. |

OTHER PUBLICATIONS

International Search Report and Written Opinion (Aug. 28, 2020) Application No. PCT/US20/36906.

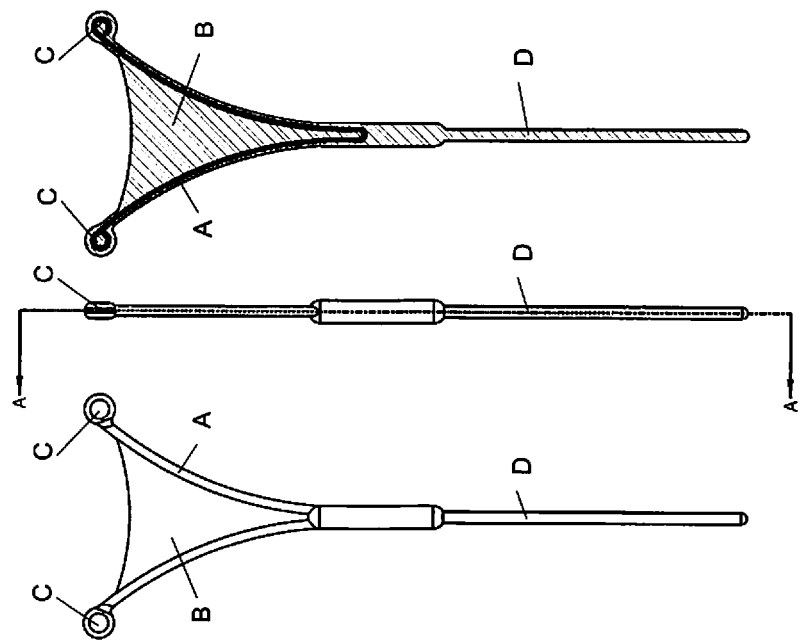

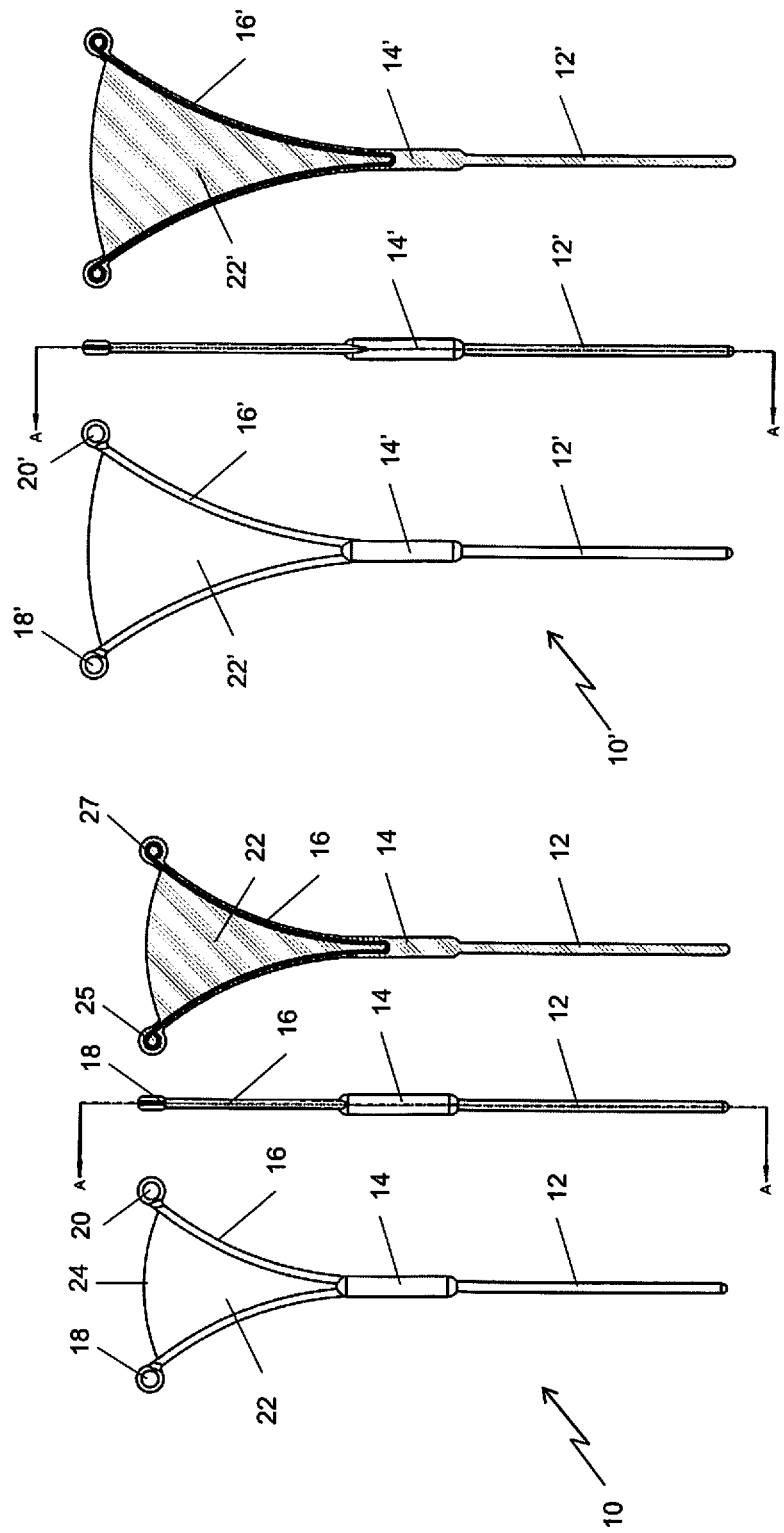

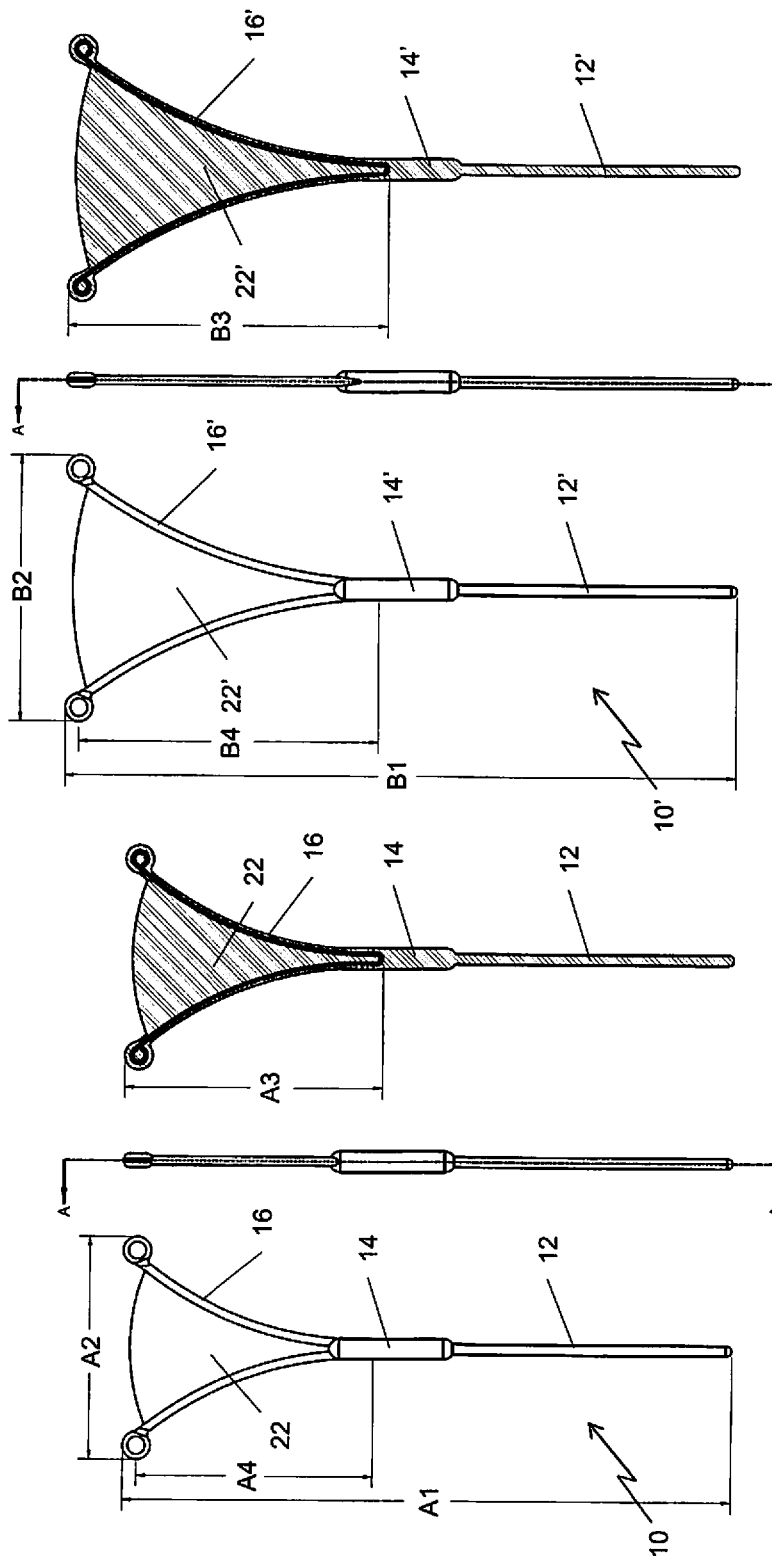

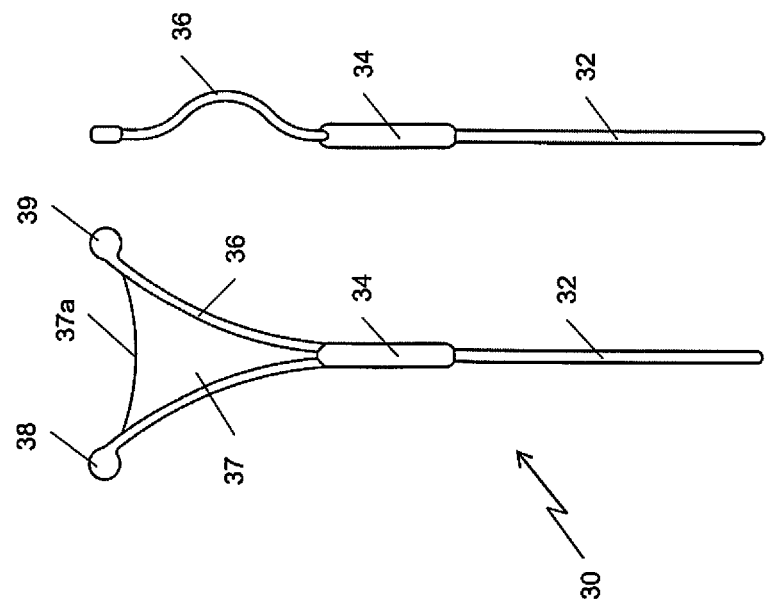

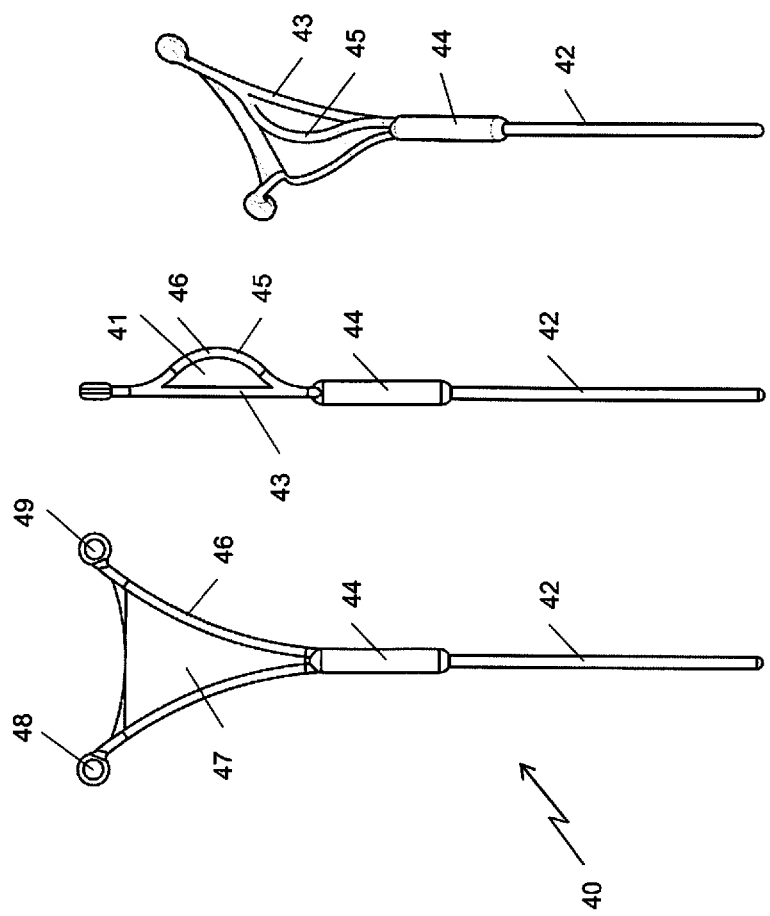

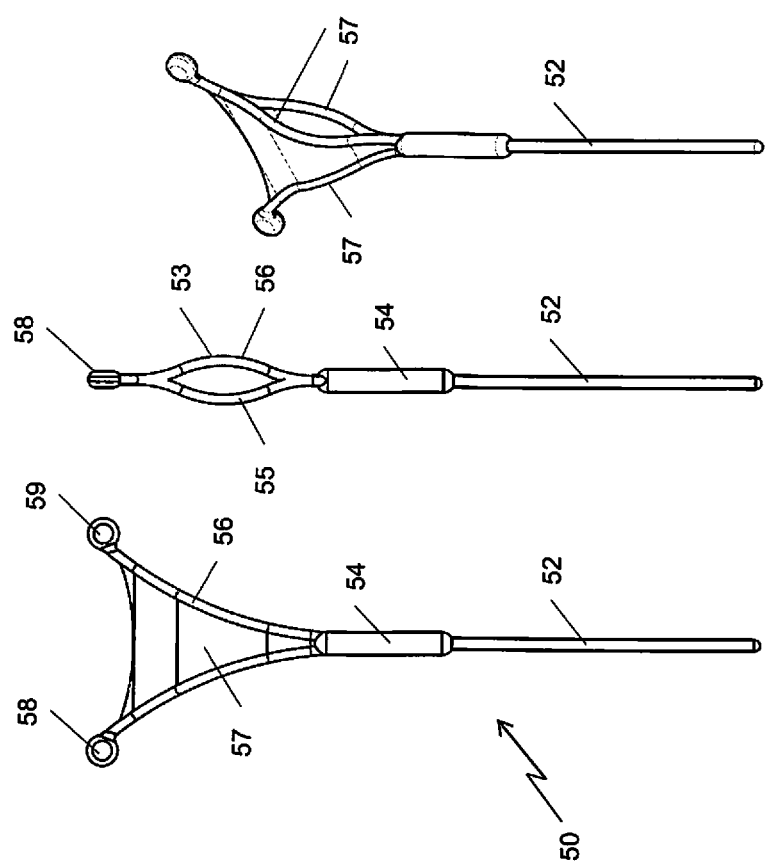

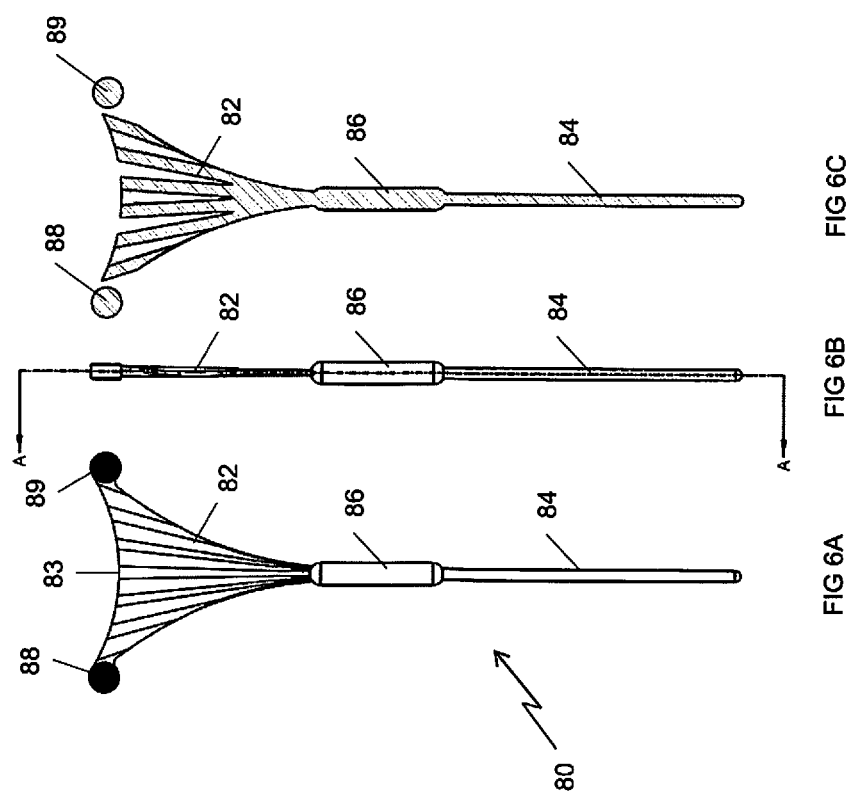

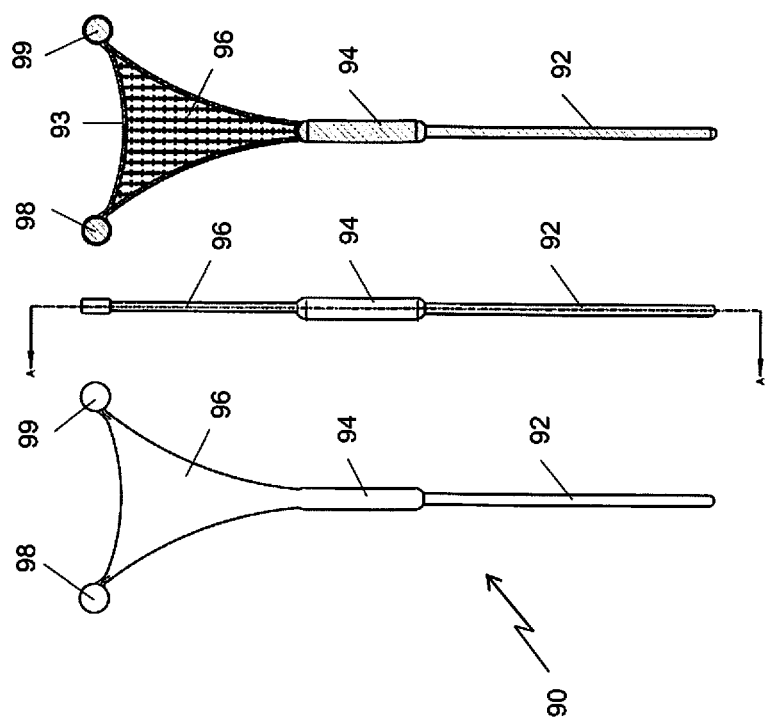

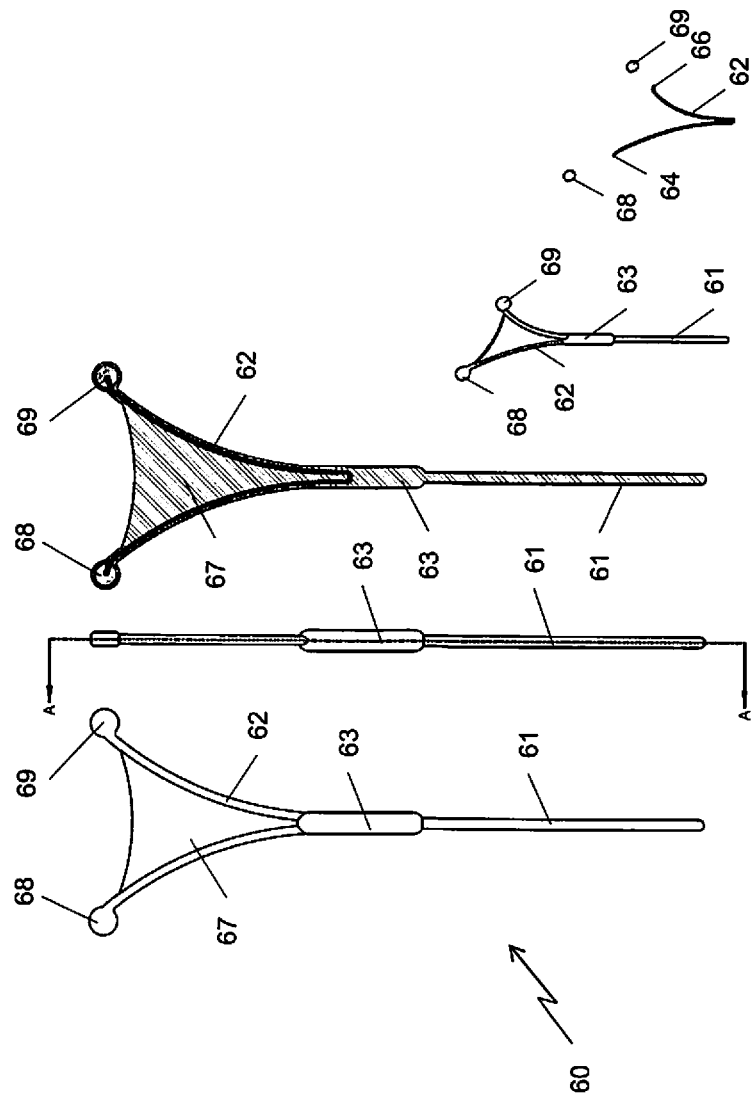

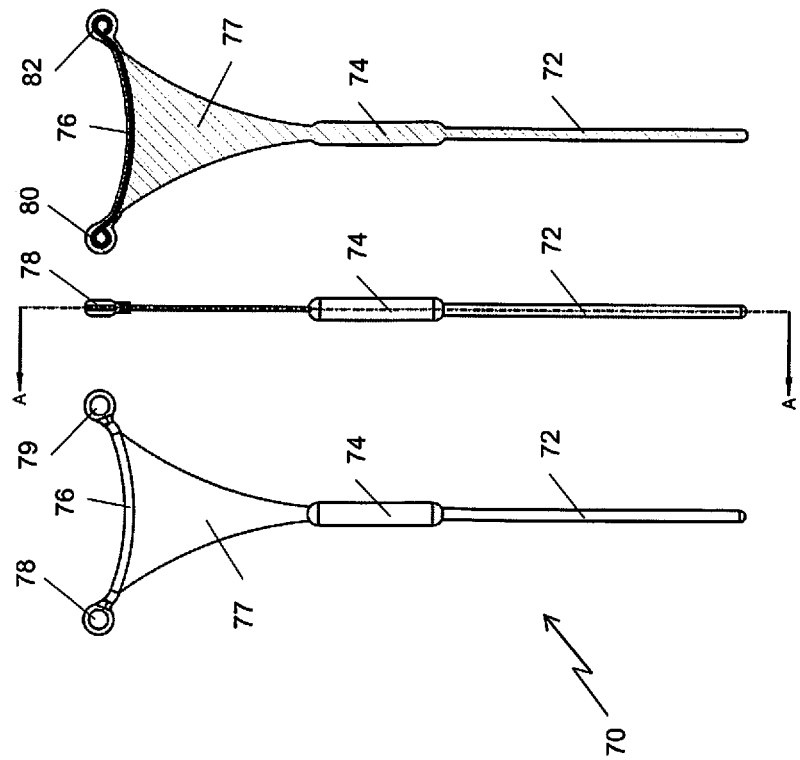

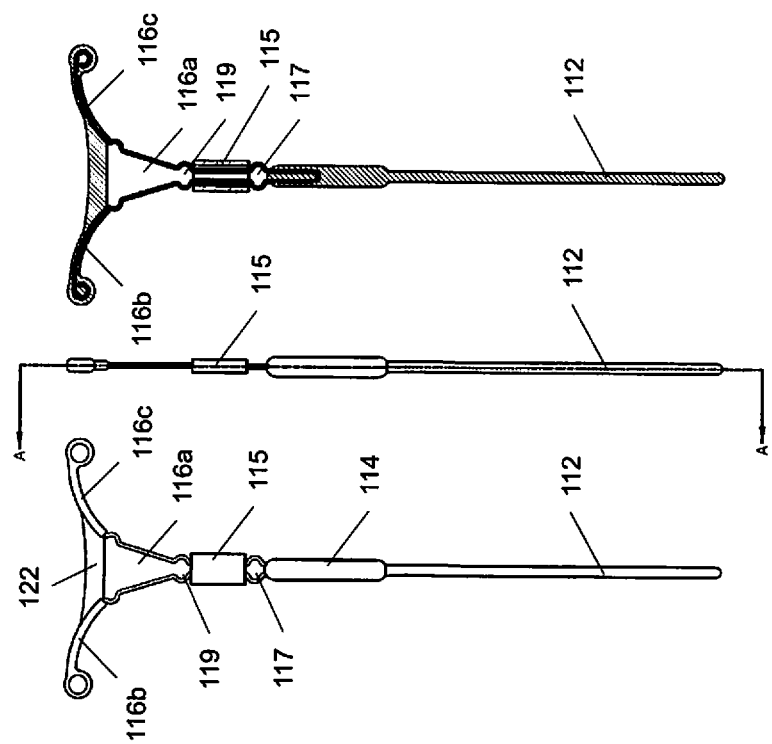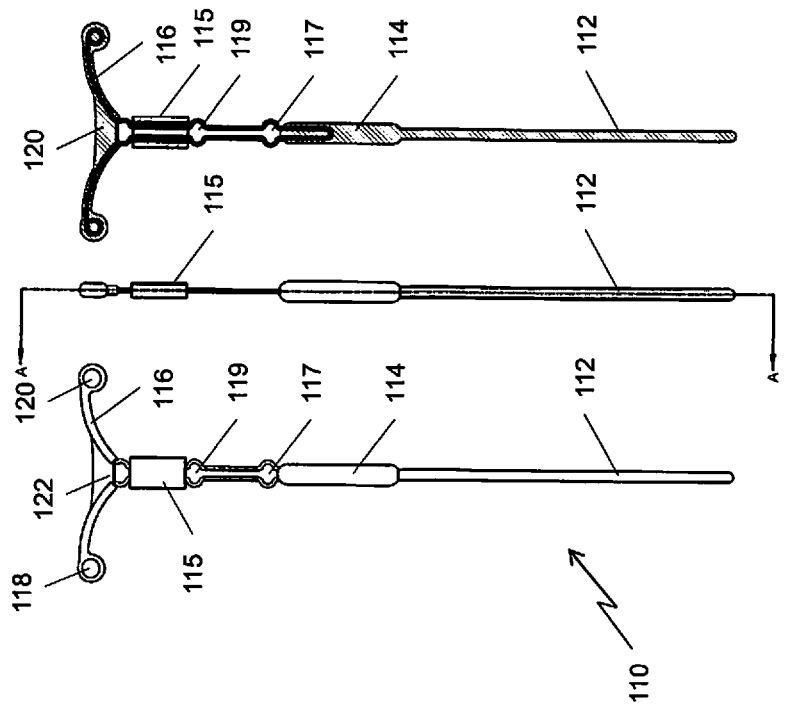

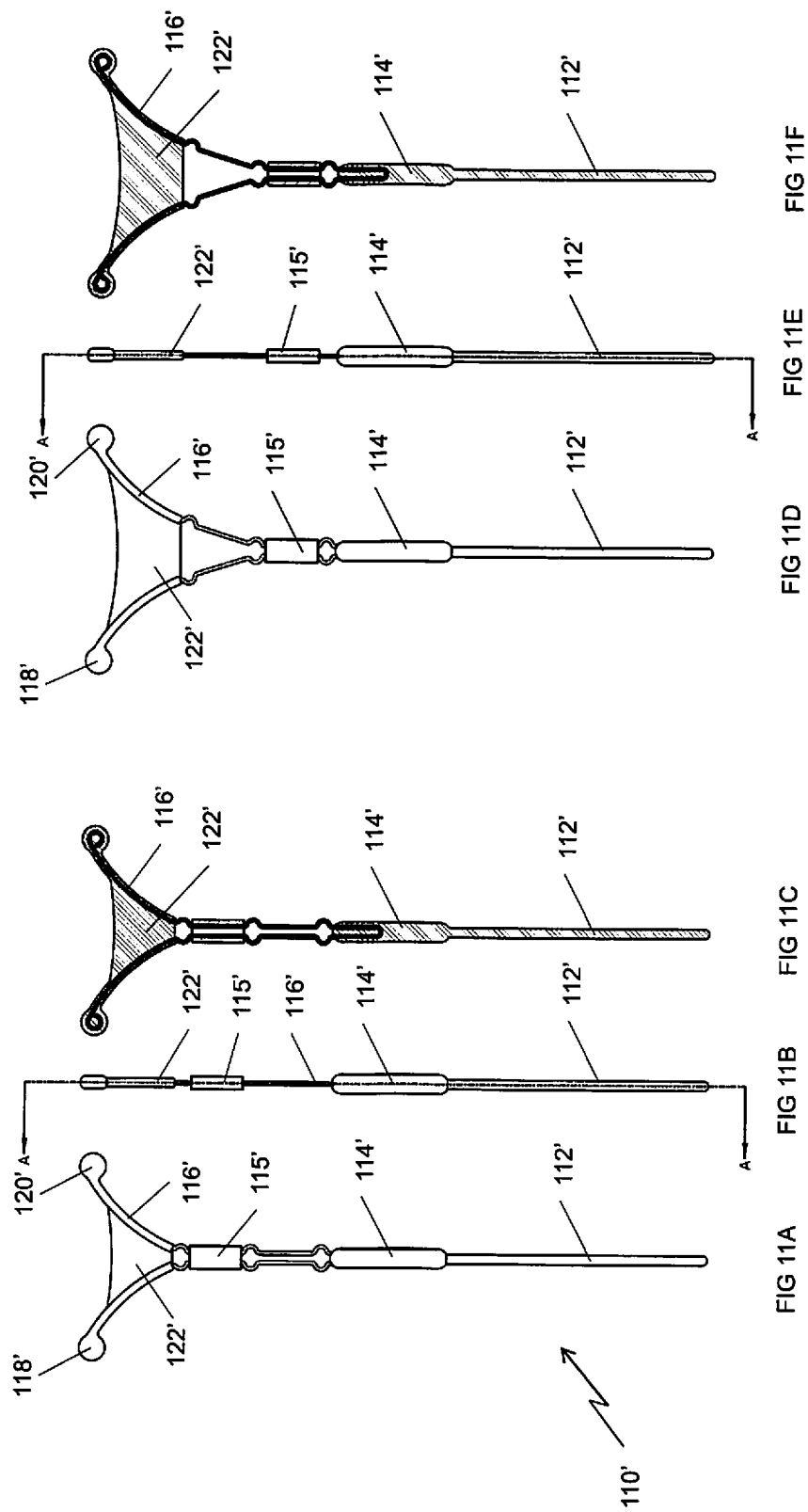

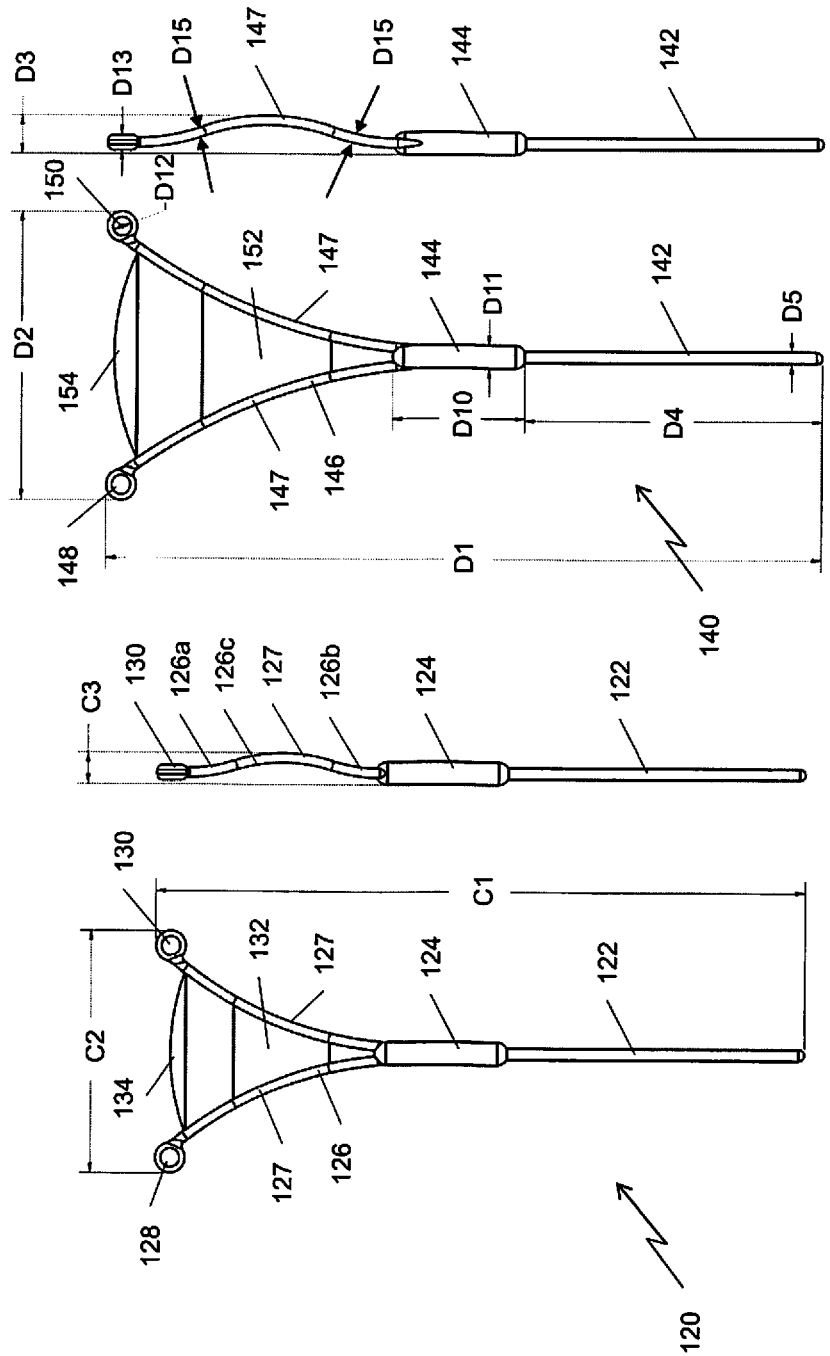

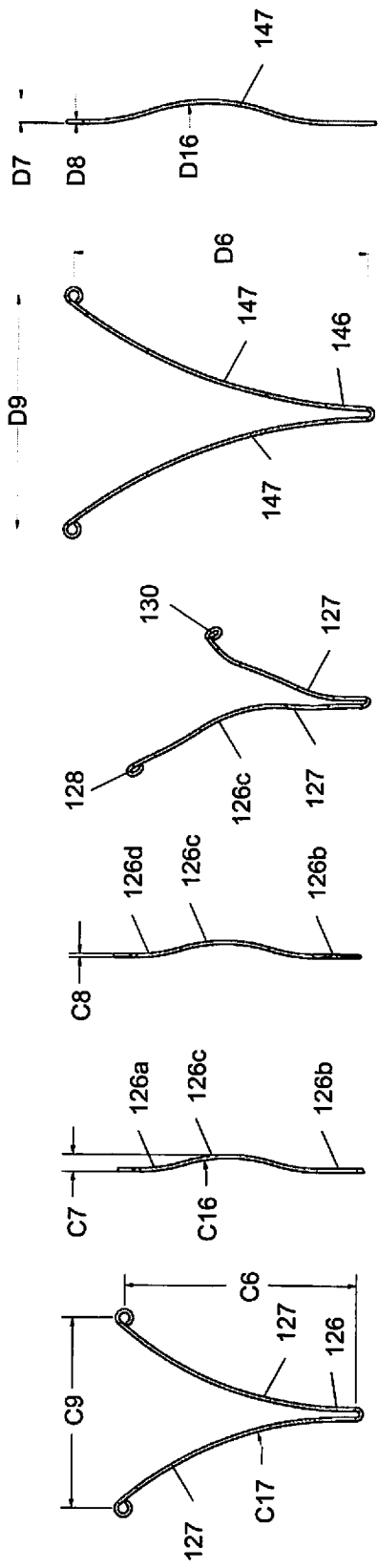

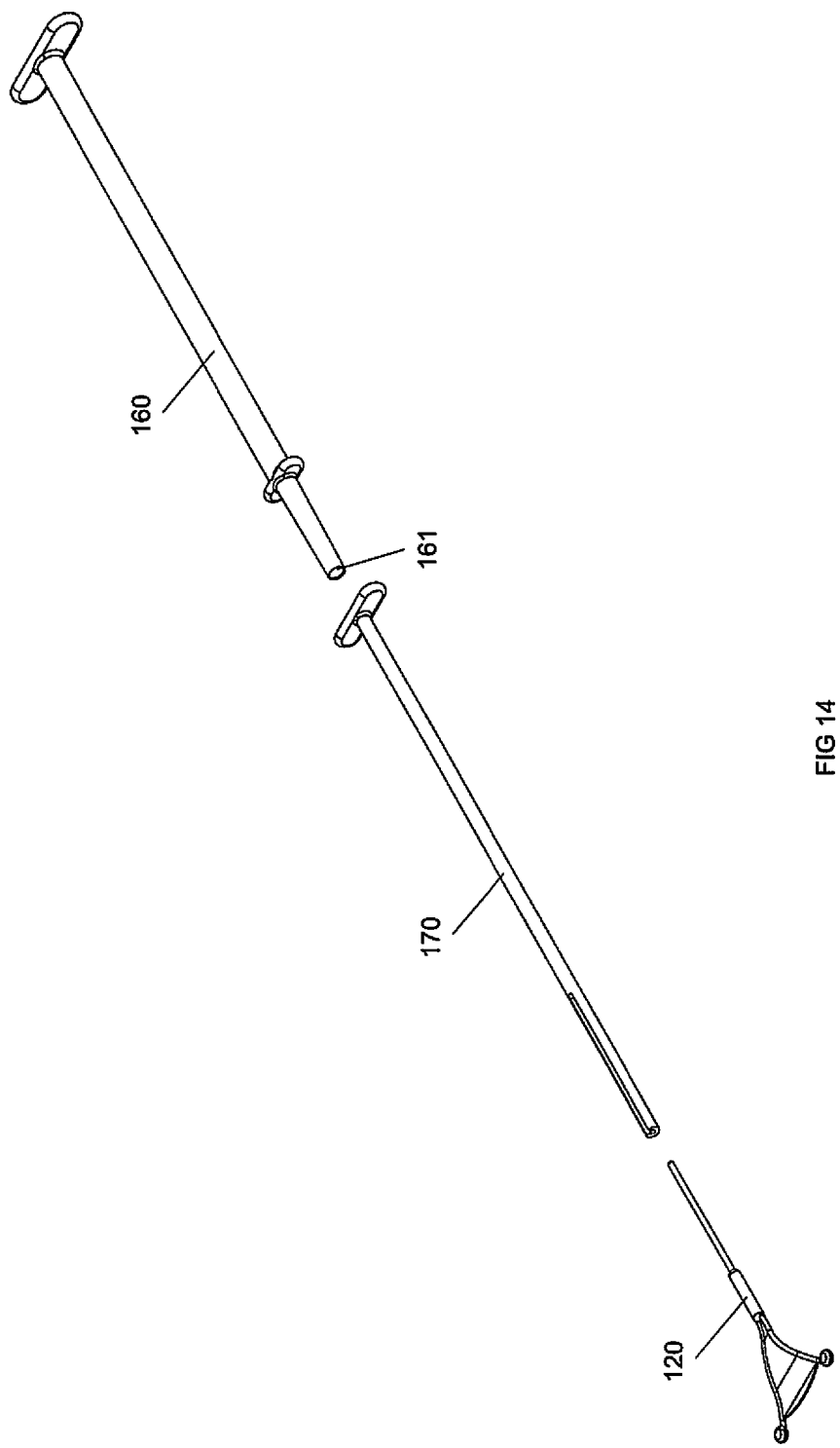

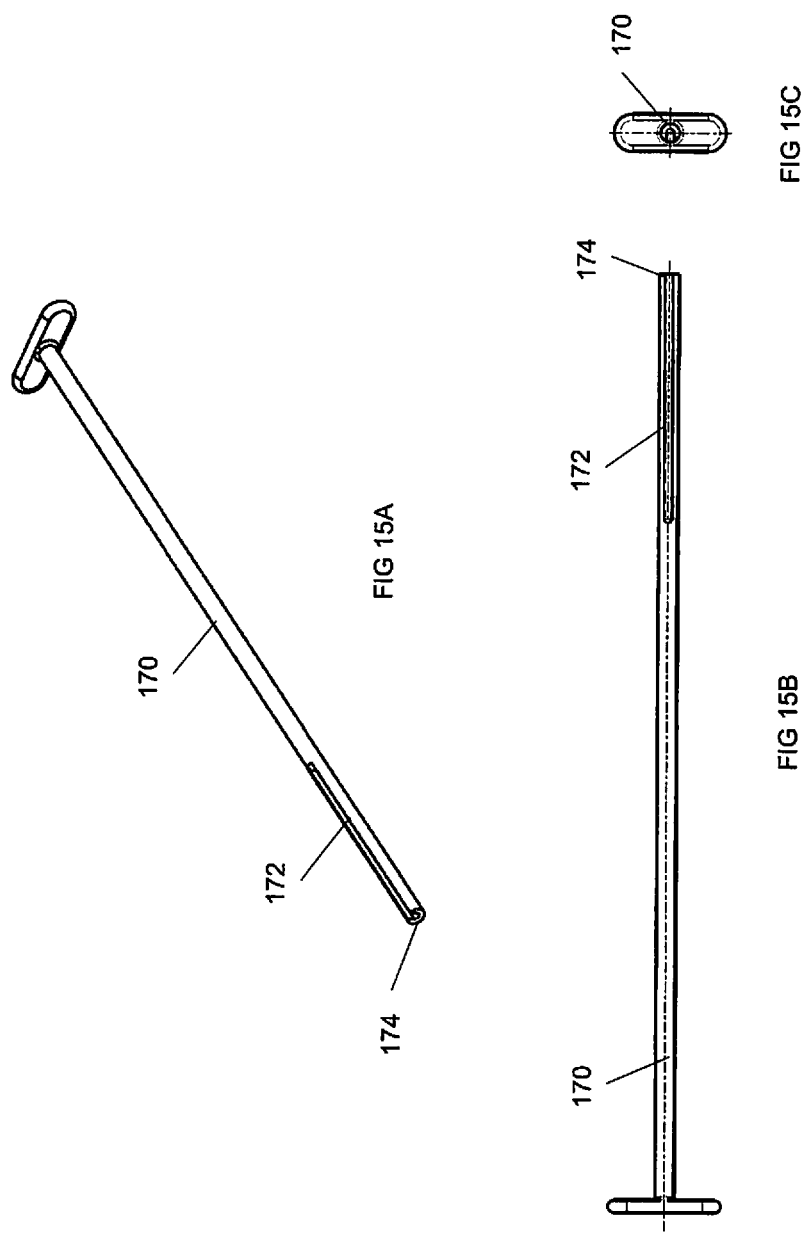

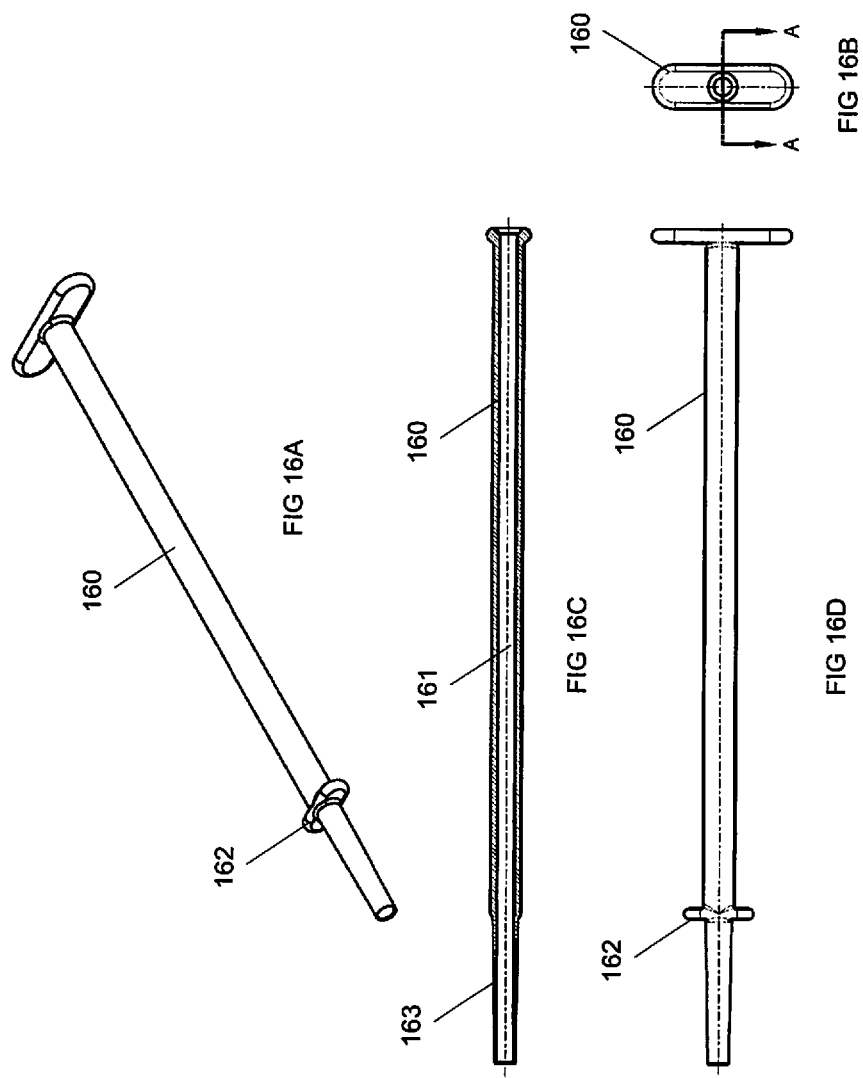

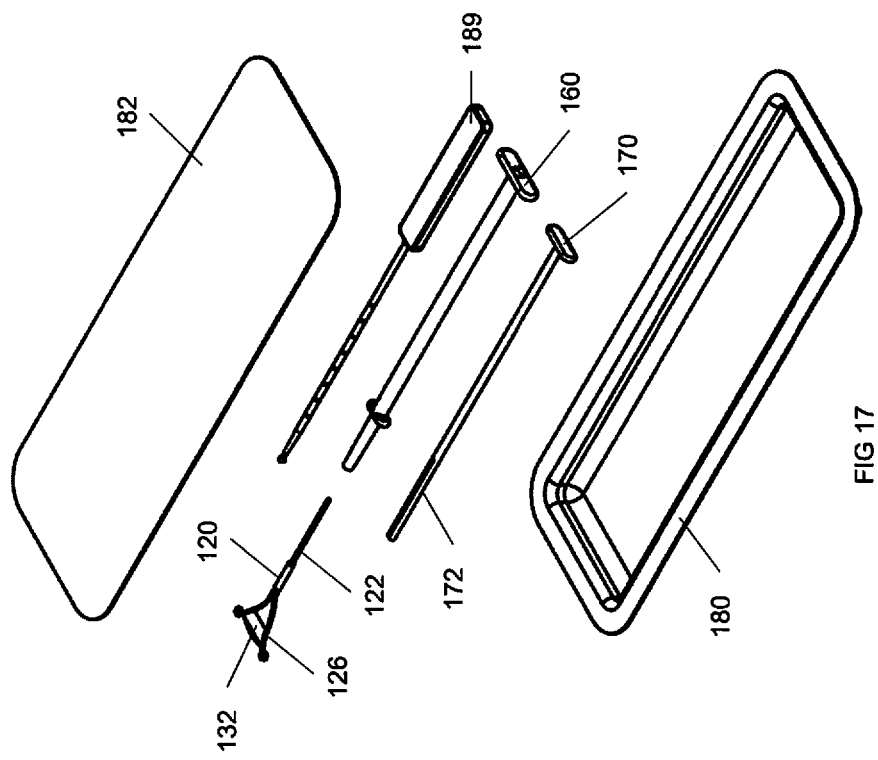

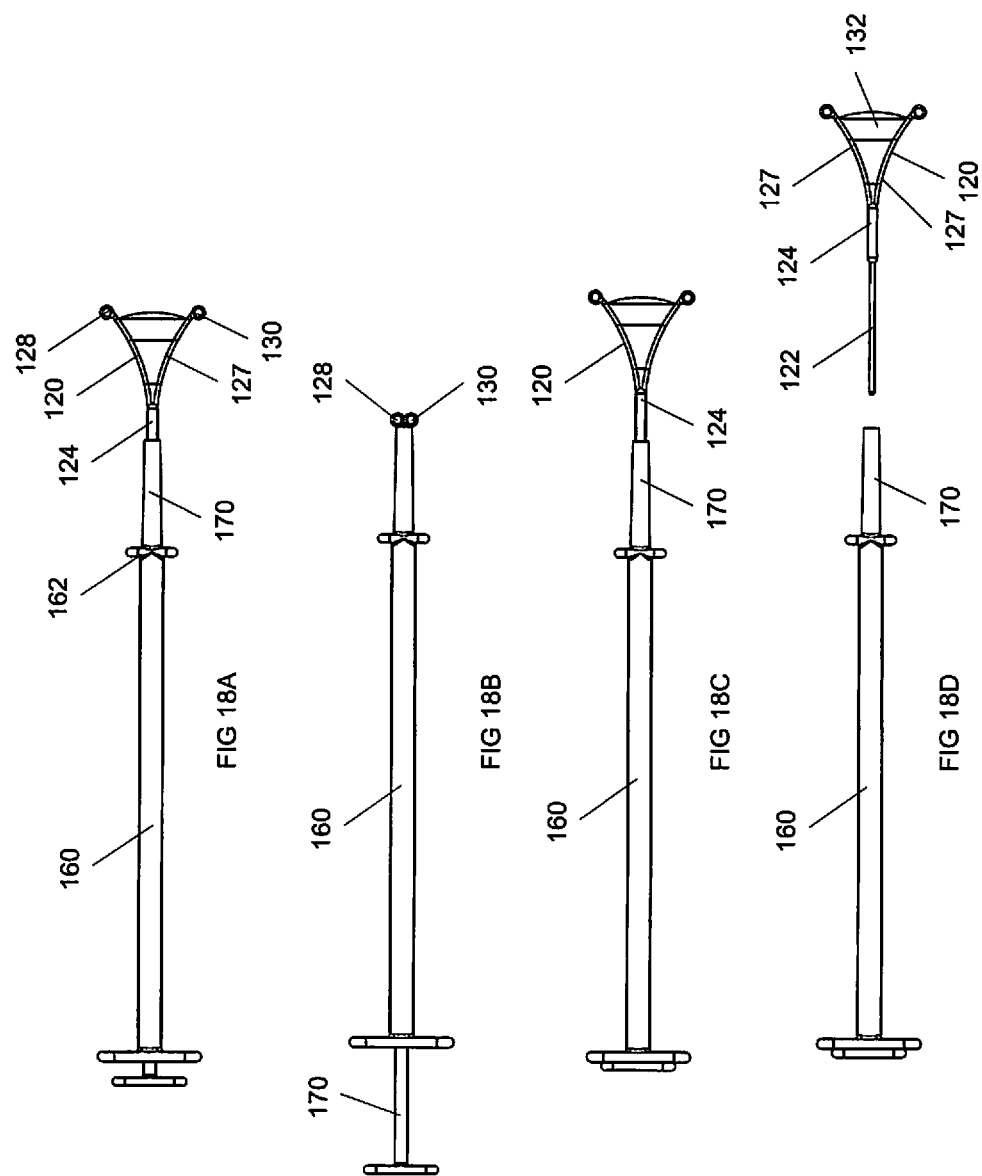

INTRAUTERINE DEVICE

This application is a 371 of International application serial no. PCT/US20/36906, filed Jun. 10, 2020, which claims priority to provisional application 62/862,056, filed Jun. 15, 2020. The entire contents of each of these applications are incorporated herein by reference.

BACKGROUND

Technical Field

This application relates to an intrauterine device inserted into the uterine cavity to prevent egg fertilization.

Background

Intrauterine devices (IUD) which are inserted into the uterine cavity to prevent egg fertilization are known. The IUD as a foreign body interferes with human reproduction through a localized inflammatory reaction of the endometrial and myometrial functions of the uterus. Cellular and humoral immune-inflammatory responses mediate the localized inflammation. Many IUDs use the hormone progestin which is released to prevent sperm from fertilizing eggs. Other common IUD's are composed of copper, which affects sperm cells through the release of copper ions which are toxic to sperm and also cause the uterus and fallopian tubes to produce a fluid which is also toxic to sperm, Copper and hormonal IUDs have active ingredients that are absorbed by the body thereby creating additional localized changes as a result of hormonally related changes to secretions and spermicidal affects.

When an IUD is placed, the endometrial surface layers are eroded down to the basement membrane. This effect is more pronounced with larger IUDs and when there is greater contact area to the endometrium. The erosion of the endometrial surface layers causes defects in the vascular epithelium, hemorrhages unchecked by hemostasis, and direct bleeding from the ulcerated areas in contact with the IUD. In IUD users, this affects the entire genital tract because of luminal transmission of the fluids that accumulates in the uterine lumen. The immune-inflammatory response affects events prior to implantation, specifically ovum development in the tubes, sperm migration, and ovum transport in the uterus. It also affects the function or viability of gametes, decreasing the rate of fertilization and lowering the chances of survival of any embryo that may be formed, even before it reaches the uterus.

However, there are drawbacks with copper IUDs such as allergies and heavier periods. Drawbacks of hormonal IUDs include missed periods, bleeding and spotting between periods, weight gain, acne, increased risk of idiopathic intracranial hypertension, and increased adverse effects for women with a history of some cancers. It is also inadvisable to use a hormonal IUD while breastfeeding.

SUMMARY OF INVENTION

The present invention overcomes the problems and deficiencies of the prior art. The present invention provides an intrauterine device placed within the uterine cavity to prevent egg fertilization. In the intrauterine devices of the present invention, unlike copper or hormonal IUDs, the mechanism of action is only physical contact with the endometrium. Thus, the primary mode of action is a foreign body physical contact of the device to the endometrium.

The devices of the present invention provide increased surface area to fill the uterine cavity and better conform to the uterine cavity. Several embodiments of the device are disclosed herein and discussed in detail below.

In accordance with one aspect of the present invention, an intrauterine device for preventing egg fertilization is provided including a membrane and frame having first and second arms movable from a first position and a second more expanded position, the frame supporting the membrane to move the membrane between a first position and a second more expanded position. The first and second arms are non-planar and each arm has a proximal portion, an intermediate portion and a distal portion. The first arm has a bend at the intermediate portion so the intermediate portion of the first arm lies in a different plane than the proximal portion of the first arm and the second arm has a bend at the intermediate portion so the intermediate portion of the second arm lies in a different plane than the proximal portion of the second arm. An elongated tail portion extends proximally of the membrane.

In some embodiments, the membrane has a proximal portion closer to the tail portion and a distal portion, the distal portion having a convex end.

In accordance with another aspect of the present invention, an intrauterine device for preventing egg fertilization is provided including a membrane, a frame having first and second arms movable from a first position to a second more expanded position, the frame supporting the membrane to move the membrane between a first position and a second more expanded position. The first and second arms each have a proximal portion, an intermediate portion and a distal portion. The membrane is supported between the first and second arms and has a proximal portion closer to the tail portion and a distal portion, the distal portion having a convex end. An elongated tail portion extends proximally of the membrane.

In some embodiments, the first arm terminates in a first bead and the second arm terminates in a second bead. In some embodiments, the frame has a silicone coating thereover. In some embodiments, the frame and first and second beads have a silicone coating thereover. In some embodiments, the silicone coating includes barium for radiopacity.

In some embodiments, the membrane is composed of a non-copper material.

In some embodiments, the membrane is composed of a non-reactive material.

In accordance with another aspect of the present invention, the devices of the present invention are provided in combination with a delivery system, the delivery system having an inner tube with an elongated slot to receive the tail portion of the device and an outer tube. The inner tube is positioned within the outer tube, the outer tube maintaining the frame in the first position.

In some embodiments, the outer tube and inner tube are relatively movable.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 1A is a plan view of a prior art intrauterine device,
FIG. 1B is a side view of the prior art device of FIG. 1A;
FIG. 1C is a cross-sectional view taken along line A-A of FIG. 1B;

FIG. 2A is a plan view of one embodiment of the intrauterine device of the present invention having a concave distal edge;

FIG. 2B is a side view of the device of FIG. 2A;

FIG. 2C is a cross-sectional view taken along line A-A of FIG. 2B;

FIG. 2D is a plan view of a larger size intrauterine device of FIG. 2A having a convex distal edge;

FIG. 2E is a side view of the device of FIG. 2D;

FIG. 2F is a cross-sectional view taken along line A-A of FIG. 2E;

FIGS. 2G and 2H are plan and side views, respectively, and FIG. 2I is a cross-sectional view taken along line A-A of FIG. 2H, of the device of FIG. 2A showing an example of dimensions of the device;

FIGS. 2J and 2K are plan and side views, respectively, and FIG. 2L is a cross-sectional view taken along line A-A of FIG. 2K, of the device of FIG. 2D showing an example of dimensions of the device;

FIG. 3A is a plan view of an alternate embodiment of the intrauterine device of the present invention having a non-planar side profile;

FIG. 3B is a side view of the device of FIG. 3A;

FIG. 4A is a plan view of an alternate embodiment of the intrauterine device of the present invention having a planar and a non-planar side;

FIG. 4B is a side view of the device of FIG. 4A;

FIG. 4C is a perspective view of the device of FIG. 4A;

FIG. 5A is a plan view of an alternate embodiment of the intrauterine device of the present invention having two non-planar sides;

FIG. 5B is a side view of the device of FIG. 5A;

FIG. 5C is a perspective view of the device of FIG. 5A;

FIG. 6A is a plan view of an alternate embodiment of the intrauterine device of the present invention having a frameless membrane;

FIG. 6B is a side view of the device of FIG. 6A;

FIG. 6C is a cross-sectional view taken along line A-A of FIG. 6B;

FIG. 7A is a plan view of an alternate embodiment of the intrauterine device of the present invention having a frameless mesh web;

FIG. 7B is a side view of the device of FIG. 7A;

FIG. 7C is a cross-sectional view taken along line A-A of FIG. 7B;

FIG. 8A is a plan view of an alternate embodiment of the intrauterine device of the present invention having beads as a separate component;

FIG. 8B is a side view of the device of FIG. 8A;

FIG. 8C is a cross-sectional view taken along line A-A of FIG. 8B;

FIG. 8D is a perspective view of the frame of FIG. 8A;

FIG. 8E is an exploded view of the device of FIG. 8A;

FIG. 9A is a plan view of an alternate embodiment of the intrauterine device of the present invention having a distal edge frame;

FIG. 9B is a side view of the device of FIG. 9A;

FIG. 9C is a cross-sectional view taken along line A-A of FIG. 9B;

FIG. 10A is a plan view of an alternate embodiment of the intrauterine device of the present invention having an adjustable size and shown in the smaller configuration with the collar in the distal position with the equivalent perimeter of FIG. 2A;

FIG. 10B is a side view of the device of FIG. 10A;

FIG. 10C is a cross-sectional view taken along line A-A of FIG. 10B;

FIG. 10D is a view similar to FIG. 10A showing the device in the larger configuration with the collar in the proximal position;

FIG. 10E is a side view of the device of FIG. 10D;

FIG. 10F is a cross-sectional view taken along line A-A of FIG. 10E;

FIG. 11A is a plan view of another alternate embodiment of the intrauterine device of the present invention having an adjustable size and shown in the smaller configuration with the collar in the distal position with the equivalent perimeter of FIG. 2D;

FIG. 11B is a side view of the device of FIG. 11A;

FIG. 11C is a cross-sectional view taken along line A-A of FIG. 11B;

FIG. 11D is a view similar to FIG. 11A showing the device in the larger configuration with the collar in the proximal position;

FIG. 11E is a side view of the device of FIG. 11D;

FIG. 11F is a cross-sectional view taken along line A-A of FIG. 11E;

FIG. 12A is a plan view of an alternate embodiment of the intrauterine device of the present invention having a non-planar side profile and a convex distal edge (end);

FIG. 12B is a side view of the device of FIG. 12A;

FIG. 12F is a plan view of a larger size intrauterine device of FIG. 12A;

FIG. 12G is a side view of the device of FIG. 12C;

FIG. 13A is a plan view of the membrane support structure (frame) of the intrauterine device of FIG. 12A;

FIGS. 13B and 13C are side views of the frame of FIG. 13A;

FIG. 13D is a perspective view of the frame of FIG. 13A;

FIG. 13E is a plan view of the frame of the intrauterine device of FIG. 12F;

FIG. 13F is a side view of the frame of the intrauterine device of FIG. 12F;

FIG. 14 is a perspective view of the intrauterine device and the delivery system;

FIG. 15A is a perspective view of the inner delivery tube of the delivery system of FIG. 14;

FIG. 15B is a plan view of the inner delivery tube of FIG. 15A;

FIG. 15C is a front view of the inner delivery tube of FIG. 15A;

FIG. 16A is a perspective view of the outer delivery tube of the delivery system of FIG. 14;

FIG. 16B is a front view of the outer delivery tube of FIG. 16A;

FIG. 16C is a cross-sectional view taken along line A-A of FIG. 16B;

FIG. 16D is a plan view of the inner delivery tube of FIG. 16A;

FIG. 17 is a perspective view of the intrauterine delivery device, the components of the delivery system and the packaging for the device and delivery components;

FIG. 18A is a side view of the intrauterine device of FIG. 12A in a partially deployed position;

FIG. 18B is a side view of the delivery system of FIG. 14 with the inner tube in the retracted position;

FIG. 18C is a view similar to FIG. 18B showing the inner delivery tube advanced within the outer tube to deploy the intrauterine device; and FIG. 18D is a view similar to FIG. 18c showing the intrauterine device released from the delivery system.

DESCRIPTION OF PREFERRED EMBODIMENTS

Figures 12C, 12D, 12E:
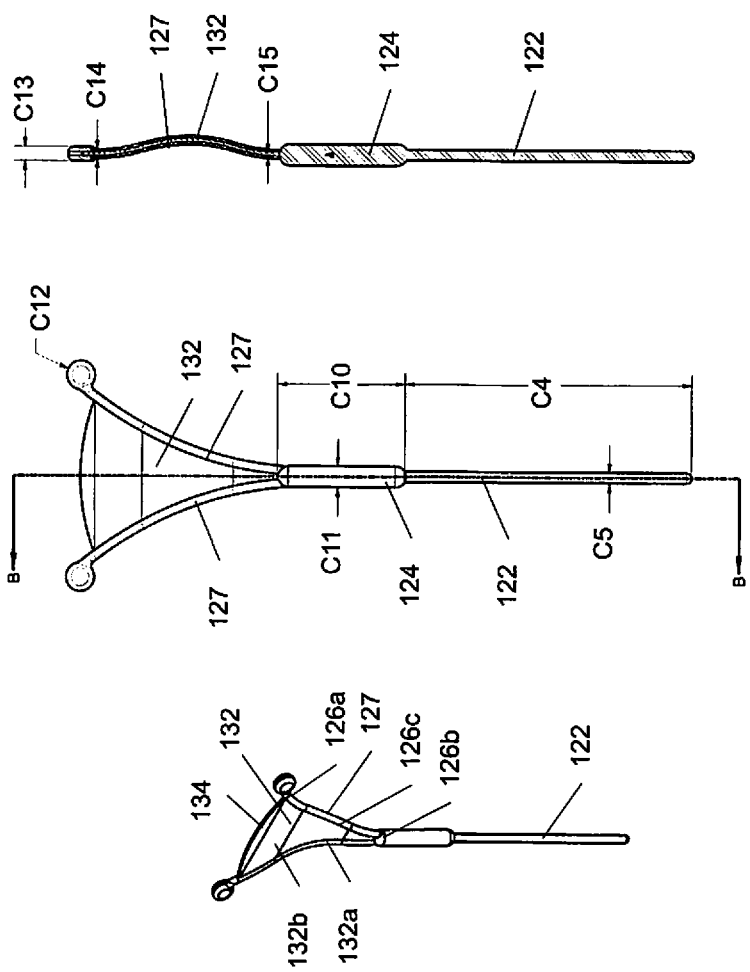
FIG. 12C is a perspective view of the device of FIG. 12A.
FIG. 12D is a plan view of the intrauterine device of FIG. 12A to illustrate various dimensions of the device.
FIG. 12E is a longitudinal cross-sectional view taken along line B-B of FIG. 12D.

The present invention provides non-hormonal intrauterine devices inserted into the uterine cavity to prevent egg fertilization. Various embodiments of the devices, as well as various sizes, are discussed in detail below. The intrauterine devices of the present invention provide a foreign body physical contact, and unlike copper or hormonal IUDs, are non-reactive and rely only on physical contact with the endometrium. The devices of the present invention provide increased surface area to fill the uterine cavity and better conform to the uterine cavity.

The devices of the present invention include a tail portion and a membrane or web that is inserted into the uterine cavity in a collapsed position and expands within the uterine cavity to fill a large space within the cavity. In some embodiments, a frame attached or embedded in the membrane causes expansion; in other embodiments the membrane itself is made of self-expanding material (referred to herein as "frameless"). Each of these versions is discussed in detail below.

The devices exert an expansive force to stretch from end to end of the uterus. The devices further exert a non-migratory force to prevent dislodgement. In preferred embodiments, the device can remain in the cavity for a five to ten year period, although other insertion time periods are also contemplated.

In some embodiments, the devices can come in two or more sizes. These are referred to herein as "non-adjustable" devices. In other embodiments, the device itself can be adjusted to two, or in some embodiments, more than two, sizes. These are referred to herein as "adjustable devices." These adjustable and non-adjustable versions are discussed in detail below.

The frame for expanding the membrane (web) can be made of various materials such as stainless steel, e.g., 300 stainless steel, cobalt chrome or nickel titanium. The membrane can be made for example of ePTFE, textiles, silicone, urethane, polyurethane or siliconized polyurethane. Other materials to form the frame and membrane are also contemplated. The devices in preferred embodiments are not made of copper.

Preferred embodiments of the devices of the present invention have a soft coating to minimize trauma during insertion and long term placement. Preferred embodiments of the devices provide increased surface area to increase efficacy. These preferred embodiments are discussed in detail below.

The devices of the present invention advantageously satisfy the following parameters: 1) fill enough space in the uterine cavity to act as a blockade for eggs, i.e. prevent a fertilized egg from implanting in the wall by increasing the surface area of the membrane; 2) minimize patient discomfort; 3) are non-hormonal (inactive); and/or 4) are durable, e.g., can remain in the body for a number of years.

In some embodiments, the device can be resterilized and reinserted.

FIGS. 1A-1C illustrate a prior art intrauterine device. The device has an expandable wire frame A, a stretchable membrane B supported by the frame A, beads C at the distal tips of the frame A, and a tail portion D. The intrauterine devices of the present invention are structurally and materially different and have usage and clinical advantages over the prior art device of FIG. 1A. These features/differences of the present invention can be appreciated by the detailed discussion below of the various embodiments.

Note as used herein the term "proximal" denotes the component, region or portion closer to the user and the term "distal" denotes the component, region or portion further from the user. As used herein, the term "substantially" denotes a deviation of 15% of the numeric value.

Turning now to the drawings, and particular embodiments of the present disclosure, wherein like reference numerals identify similar structural features of the devices disclosed herein, FIGS. 2A-2C illustrate one embodiment of the intrauterine device of the present invention. The intrauterine device is designated generally by reference numeral 10 and has a tail portion 12 and an enlarged tube or sleeve 14 integral with the tail portion 12 or alternatively positioned over the tail portion 12 or alternatively attached to the tail portion 12 and extending distally therefrom. An expandable frame 16 extends from the sleeve 14 and a membrane 22 is attached to frame 16 and is expandable by the frame 16. In some embodiments, sleeve 14 and membrane 22 are the same component, constructed of the same material; in other embodiments, they are composed of separate materials. At the tips of the frame 16 are distal beads 18, 20. The device 10 is shown in FIGS. 2A-2C in an expanded position (condition).

The device 10 is inserted through an insertion tube or sleeve (not shown) with the wire frame 16 and membrane 22 in the collapsed position (condition). When exposed from the insertion tube, the frame 16 automatically expands to the expanded position (condition) shown in FIGS. 2A-2C to expand the membrane 22 within the uterine cavity.

The distal edge (end) 24 of membrane 22 is convex to provide additional surface area for the membrane 22 and to better conform to the uterine anatomy. The convex end as shown spans the width of the membrane from the first arm to the second arm. It should be appreciated that such convexity can be provided in the membranes or webs of the other embodiments disclosed herein. Note as used herein, the term "membrane" as discussed with respect to the various embodiments, denotes a material or structure that is positioned, e.g., spans an area, distal of the tail portion and configured to occupy sufficient space in the uterine cavity. Various structures and materials for the membrane, such as silicone, are discussed herein, but the membrane can be composed of other materials for placement within the cavity to perform the functions as described herein.

The frame 16 is V-shaped, with the vertex of the V at the proximal end connected to the enlarged tube 14 on tail portion 12. The arms of the V terminate in curled distal tips or loops 25, 27. The membrane 22 can extend to cover the wire loops 25, 27 to form distal beads 18, 20. Note the loops 25, 27 are circular loops to create a spherical bead, however, it should be understood that loops and/or beads of different configurations, e.g., oval, rectangular with smooth edges, asymmetric configurations, etc. can be used instead, in this embodiment of FIG. 2A as well as in the other embodiments disclosed herein. The distal beads are placed adjacent the fallopian tubes.

The device 10' of FIGS. 2D-2F is identical to device 10 of FIG. 2A except it is a larger size. Therefore, identical components have been designated with "prime" reference numerals, such that device 10' has a tail portion 12', a tube or sleeve 14', an expandable frame 16' with distal beads 18'. 20' and a membrane 22'.

Various dimensions for devices 10 and 10' are contemplated. FIGS. 2G and 2H, and the table below, show one example of dimensions for the device 10 of FIG. 2A and FIGS. 2I and 2J, and the table below, show one example of the dimensions for the device 10' of FIG. 2D. Note these dimensions are provided by way of example as other dimensions are also contemplated. Such device dimensions can also be applicable to the devices of the other embodiments disclosed herein.

Example—FIGS. 2G-2I

| FEATURE | DESIGNATION IN DRAWING | DIMENSIONS (IN MILLIMETERS) |
|---|---|---|
| Overall length | A1 | 87.3 |
| Width at frame | A2 | 28 |
| Length of Frame | A3 | 37 |
| Length (to middle of bead | A4 | 34 |

Example—FIGS. 2J-2L

| FEATURE | DESIGNATION IN DRAWING | DIMENSIONS (IN MILLIMETERS) |
|---|---|---|
| Overall length | B1 | 96.3 |
| Width at frame | B2 | 34 |
| Length of Frame | B3 | 46 |
| Length(to middle of bead) | B4 | 43 |

In the embodiment of FIG. 2A, the frame wires are planar. FIGS. 3A-5B illustrate alternate embodiments wherein the wire(s) are non-planar (see side profile) which in some applications better match the anatomy. Device 30 of FIG. 3A, like device 10 of FIG. 2A, has a tail portion 32, an enlarged tube or sleeve 34, an expandable frame 36 with distal beads 38, 39 and a membrane 37 expanded by frame 36. It has a non-planar side profile as shown in FIG. 3B. The membrane 37 has a concave distal edge 37a which provides less surface area than the convex edge of membrane 22 discussed above. In alternate embodiments, the edge is convex.

The device of FIGS. 12A-12E, 13A-13D also has a non-planar side profile. Device 120, like device 10 of FIG. 2A, has a tail portion 122, an enlarged tube or sleeve (barrel) 124, an expandable V-shaped frame 126 with distal beads 128, 130 and a membrane 132 expandable by frame 126 with a convex distal edge 134 to increase surface area. The frame 126 extends from barrel 124 and is attached thereto as shown. The frame 126, preferably a wire frame, has two arms 127 each extending from tube 124, and each having a distal portion (region) 126a, a proximal portion (region) 126b and an intermediate portion (region) 126c between the proximal and distal portions 126b, 126a. The frame arms are non-linear and each has a curvature in the intermediate portion 126c so the intermediate portion 126c lies in a different plane than the distal portion 126a and in a different plane than the proximal portion 126b. The distal and proximal portions can lie in the same plane or alternatively can be in different planes. Stated another way, the intermediate portion 126c extends radially with respect to the longitudinal axis of the device (see also FIG. 12C). The curvature increases the surface area of the attached membrane 132 as the membrane 132 is non-planer as an intermediate region curves inwardly in a concave manner due to the curvature of arms 127. Thus, the intermediate region 132a of the membrane 132 lies in a different plane than the distal region 132b as shown in FIG. 13C. Note that in FIG. 12a a single curvature or arc is illustrated, however it is also contemplated that more than one curve can be provided for increased surface area. Also, the position of the curve with respect to the distal and proximal portions 126a, 126b, length of the curve and size of the curve can vary from that shown.

FIGS. 12A, 12B, 12D. 12E and 13A-13C illustrate one example of dimensions of the intrauterine device of FIG. 12A, and these dimensions are set forth in the chart below. It should be appreciated that other dimensions are also contemplated. FIGS. 12F and 12G, 13E and 13F illustrate a larger version of the device of FIG. 12A. Device 140 is identical to device 120 and has a tail portion 142, an enlarged tube or sleeve 144, an expandable frame 146 with bent (curved) arms 147 and distal beads 148, 150 and a membrane 152 with a convex distal edge 154 to increase surface area.

The tables below provide examples of the dimensions of the device 120 and 140, it being understood that other dimensions are also contemplated.

Example—FIG. 12A Embodiment (Device 120)

| FEATURE | DESIGNATION IN DRAWING | DIMENSIONS (IN MILLIMETERS) |
|---|---|---|
| Overall length | C1 | 87.3 |
| Width at widest portion | C2 | 32 |
| Height | C3 | 4.12 |
| Tail length | C4 | 40 |
| Tail diameter | C5 | 1.5 |
| Frame length | C6 | 34 |
| Frame Height | C7 | 2.5 |
| Frame wire diameter | C8 | .025 |
| Frame width span (without coating) | C9 | 28 |
| Barrel length | C10 | 17.78 |
| Barrel diameter | C11 | 3 |
| Bead diameter | C12 | 4 |
| Bead thickness' | C13 | 2 |
| Frame diameter | C14 | 1.25 |
| Web thickness | C15 | .5 |
| Arm Radius | C16 | 21.38 |
| Arm Radius | C17 | 49.75 |

Example—FIG. 12F Embodiment (Device 140)

| FEATURE | DESIGNATION IN DRAWING | DIMENSIONS (IN MILLIMETERS) |
|---|---|---|
| Overall length | D1 | 96.3 |
| Width at widest portion | D2 | 38 |
| Height | D3 | 5.12 |
| Tail length | D4 | 40 |
| Tail diameter | D5 | 1.5 |
| Frame length | D6 | 43 |
| Frame Height | D7 | 3.5 |
| Frame wire diameter | D8 | .025 |
| Frame width span (without coating) | D9 | 34 |
| Barrel length | D10 | 17.78 |
| Barrel diameter | D11 | 3 |
| Bead diameter | D12 | 4 |
| Bead thickness | D13 | 2 |
| Frame diameter | D14 | 1.25 |

| FEATURE | DESIGNATION IN DRAWING | DIMENSIONS (IN MILLIMETERS) |
|---|---|---|
| Web thickness | D15 | .5 |
| Arm Radius | D16 | 26.02 |

The device 120 (and 140) can be formed by various methods such as i) overmolding the wire form (V-shaped frame) to match the shape of the wire form; ii) dip molding to match the shape of the wire form; or iii) not initially shaping the wire form and molding it in a flat configuration and bending it once coated. In this latter method, the loops can be formed at the end of the V but the arms are not bent out of the plane to increase to the D3 dimension until after overmolding (or dip molding). Note other manufacturing methods are also contemplated.

Device 40 of FIG. 4A, like device 10 of FIG. 2A, has a tail portion 42, an enlarged tube or sleeve (barrel) 44, an expandable V-shaped frame 46 with distal beads 48, 49 and a membrane 47 expandable by frame 46. The frame 46, as shown in the side profile of FIG. 4B, has a planar arm 43 and a non-planar arm 45 with a gap 41 therebetween. Arm 45 is non-linear and has a curvature or bend as shown, forming a C-shape. The frame thus can have one or two straight arms 43 and one or two bent arms 45 which provide a bend in the attached membrane 47 so the membrane 47 extends inwardly in a concave manner to increase surface area. Arms 43 and 45 can be the same or separate components. Such configuration can add an anti-migratory force with thickness in addition to increasing the surface area of membrane 47. Note the material (membrane) is removed from the view in FIG. 4B (and FIG. 5B) for clarity to show the frame configuration.

Device 50 of FIG. 5A, like device 10 of FIG. 2A, has a tail portion 52, an enlarged tube or sleeve (barrel) 54, an expandable frame 56 with distal beads 58, 59 and a membrane 57 expandable by frame 56. It has two non-planar sides 53 and 55. That is, frame 56 has multiple arms 57 which are bent to provide one or more bends/curves in membrane 57 so that membrane 57 extends in multiple planes. This structure can reduce migration and increase surface area. The sides 53, 55 can be the same or separate components and lie in a different plane than the distal and proximal portion of the frame 56. With the arms in multiple planes, the membrane can extend around the top, both sides (gap between the arms) and bottom. That is, the membrane can be considered to have four panels (covers) extending between the arms—top panel, bottom panel and two side panels creating a more three dimensional membrane and thus surface area. Such four panels can also be provided between the arms in the device 40 of FIG. 4A to increase the surface area.

Device 120 and 140, as well as the other devices disclosed herein, can be formed of a metal frame overmolded with silicone to form the membrane and beads. The membrane material can be radiopaque, e.g., can contain barium or other materials. The coating can also form the collar (barrel) and tail of the device. The silicone coating provides a softer less traumatic device with no sharp edges. The frame can be made of stainless steel, Nitinol (nickel-titanium alloy) or a material of sufficient springiness to self-expand to expand the membrane. It could also be made of shape memory Nitinol that transitions to its shape memorized condition (position) due to a change in temperature, e.g., exposure to body temperature or due to release of a constraining tube. The wire form can be made of radiopaque materials such as platinum and platinum iridium, tantalum and tantalum-tungsten and similar alloys in clad composite with 316LVM stainless steel, nitinol and MP35N.

The beads of FIGS. 2A-5B are shown as integral as the wire frame is looped at the distal ends of the arms, and the membrane attached thereover, to form the beads. In an alternate embodiment shown in FIGS. 8A-8E, the beads 68, 69 of device 60 are separate components welded or attached by other methods to the non-looped distal ends of the expandable frame 62. Making the beads as a separate component enables the beads to be made of a more radiologically opaque material to better locate them. In this embodiment, the wire frame 62 does not roll around to form the beads. The beads 68, 69 are preferably formed of a metallic material and attached to distal tips 64, 66 of the arms of the V-shaped wire frame 62. The membrane 67 of device 60 is supported and expanded by the frame 62 and has a concave distal edge rather than a convex edge, although alternatively, the distal edge can be convex. Note such concave edge can be provided in the membranes or webs of the other embodiments disclosed herein. In all other respects, device 60 is the same as device 10, with the wire frame 62 extending from barrel 63 on tail portion 61 and expandable into the aforedescribed V-shape to spread the membrane 67 when exposed from the insertion tube as described herein. It should be appreciated that the beads as a separate component (or alternatively as integral with the wire frame) can be utilized in any of the embodiments described herein.

In the foregoing embodiments, the wire frame forms a V-shape and is attached to or positioned. e.g., embedded in, sides of the membrane such as by overmolding. That is, the two arms of the "V" extend distally and radially outwardly from the barrel to extend through and/or support opposing side edges of the membrane. (The membrane can be attached to an outer surface of the arms or the arms can be embedded in the membrane). In an alternate embodiment, the wire frame is positioned only along a distal edge of the membrane and not on the side edges. This is shown for example in FIGS. 9A-9C. Wire frame 76 of device 70 is spaced distally and unattached to barrel 74 on tail portion 72 and provides the expansive force as it extends horizontally (transverse) to a longitudinal axis of the device. It extends across the distal region or distal edge of membrane 77 and has looped ends 80, 82 forming, with the membrane, beads 78, 79. (The membrane 77 can be attached to an outer surface of the wire 76 or the wire 76 can be embedded in the membrane 77). The frame 76 bends inwardly as shown to provide the membrane 77 with a concave distal edge, however, in alternate embodiments to increase surface area, it can bend outwardly to provide the membrane 77 with a convex distal edge.

When inside the insertion tube, the wire 76 of device 70 is collapsed to a narrow U or V-shape, with the two "arms" of the U extending substantially parallel. When exposed from the delivery device, the frame 76 expands to the curved position shown. In an alternate embodiment, instead of the wire, the membrane itself can have a reinforced distal edge to provide the expansive force on the membrane to expand the membrane. It should be appreciated that the wire supporting the side edges, the wire supporting the distal edge and the wireless version can be utilized in any of the various membrane embodiments disclosed herein. It should also be appreciated that other shaped wire frames, e.g., extending along the sides and the distal edge, forming a triangular configuration or closed loop, or at other regions of the membrane are also contemplated for the various devices disclosed herein.

In the foregoing embodiments, expandable wire frames are utilized to expand the membrane thereby providing an outward force to anchor the beads. In alternate embodiments, devices without frames ("frameless devices") are provided, relying on the material itself to expand when exposed from the insertion (delivery) tube to provide the outward force to spread and to anchor the beads. This is shown for example in FIGS. 6A-6C. Frameless device 80 has a membrane 82, also referred to as a web, in the form of a folding fan, with the folding hinges of the fan applying the expansive force. The membrane 82 is inserted in the collapsed position (condition) through an insertion (delivery) sleeve or tube and when exposed from the sleeve expands to the expanded condition shown in FIG. 6A. Beads 88, 89 are integrated into the web 82 or alternatively attached to the web 82 at the distal outer ends. The web 82 can be composed of shape memory metal such as nitinol or shape memory polymer with a shape memorized expanded position which can transition in response to temperature change or removal of a constraint, e.g., a delivery tube. For example it can be laser cut out of a Nitinol sheet and shape set in a fan. Other self-expanding materials are also contemplated. The web 82 can be overmolded with a material such as silicone to smooth it. The edges of the web 82 can be rolled to smooth out the edges. In some embodiments, it could be pleated. Device 80 has an enlarged tube (barrel) 86 on tail portion 84 similar to tail portion 12 and barrel 14 of FIG. 2A. The web 82 has a concave distal edge 83 as shown but alternatively can have a convex distal edge as in FIG. 12A.

FIGS. 7A-7C illustrate an alternate embodiment of a frameless design. Device 90 has a mesh 96 extending distally of enlarged sleeve (barrel) 94 of tail portion 92. The meshed web 96 creates an expansive force. Beads 98, 99 are integrated into the web 96 or alternatively attached to the web 96 at the distal outer ends. The membrane overlays the mesh either by fusing to the web or laying it overtop the mesh (unfused). For example a silicone or urethane can overlay the mesh, surrounding the mesh in a sock-like fashion. Note the border of the mesh, i.e., the side edges, are depicted in darker lines (a hard border) for clarity to depict the outline of the mesh. The line can also be considered to depict the termination of the loose end of the mesh in some embodiments. The web 96 has a concave distal edge 93 as shown but alternatively can have a convex distal edge as in FIG. 12A.

Note the frameless devices 80 and 90, as well as the other devices disclosed herein, can have a non-planar frame as in the embodiments of FIGS. 3B, 4B, 5B and 12B.

The foregoing devices can be provided in different sizes. e.g., different lengths of the tail portion, different widths of the expanded membrane, etc. The present invention also provides devices of adjustable web sizes so the clinician can adjust the device as desired to accommodate varied uterus anatomy. Two examples of expandable devices are shown in FIGS. 10A-11F. Although FIGS. 10-11F appear to have smaller webs/membranes, this is for clarity. The devices of FIGS. 10A-11F can have equivalent membrane surface area to the aforementioned devices. The devices can also have non-planar frames as in the devices discussed above.

Turning first to the embodiment of FIGS. 10A-10C, device 110 has a tail portion 112, an enlarged tube or sleeve (barrel) 114 positioned over the tail portion 112, an expandable frame 116 extending from the sleeve 114 and a membrane 122 expandable by the frame 116. At the tips of the frame 114 are distal beads 118, 120.

An adjustable collar 115, having a lumen to receive the wire frame 116, is slidable along the wire 116 between two positions. The collar 115 is shown in FIGS. 10A-10C in the distal position and in FIGS. 10D-10F in the proximal position. The device 110 is shown in FIGS. 10A-10C in a first smaller expanded position (condition) corresponding to the collar 115 being in the distal position. The device 110 is inserted through an insertion tube or sleeve (not shown) with the wire frame 116 and membrane 122 in the collapsed position (condition) and when exposed from the insertion tube, the frame 116 automatically expands to the smaller expanded condition shown in FIGS. 10A-10C to expand the membrane 122 since the collar 115 is in the distal position.

If a larger size membrane/web is desired, with a larger transverse dimension to cover increased area within the uterine cavity, the collar 115 is retracted to the proximal position of FIGS. 10D-10F. Such retraction releases more of the wire frame (region 116a) allowing the arms 116b. 116c of the wire frame 116 to open in a longer and wider "V" to provide a second expanded position. The wire frame 116 has proximal and distal looped regions 117, 119 respectively, to act as stops for the adjustable collar 115. That is, when the adjustable collar 115 is in the distal position, the distal looped region 119 prevents proximal movement of the collar 115 unless a sufficient proximal force is applied to override the distal looped region 117. When the collar 115 is in the proximal position, proximal looped region 117 limits proximal movement of the collar 115 and distal looped region 119 limits distal movement of the collar 115 unless a sufficient distal force is applied to the collar 115 by the clinician to override the loop region 119 and move the frame 116 and membrane 122 to the smaller expanded position of FIG. 10A. Thus, prior to insertion into the uterine cavity, the user can place the collar 115 in the desired position for small or large applications. In either position, the device 110 is inserted through an insertion tube or sheath with the wire frame 116 and membrane 122 in the collapsed insertion position. When exposed from the sheath, the frame 116 expands to either the first expanded position or the second expanded position, depending on the preset position of the collar 115. The device 110 in some embodiments can include an extension extending proximally form the collar 115, such as a tube, that is accessible to the clinician at a proximal region when the device 110 is inserted in the uterine cavity. This would enable adjustment of the size of the device 110 by movement of the collar 115 when the device 110 is already positioned within the uterine cavity or pre-insertion. The device 110 can be packaged with the collar 115 in either the distal or the proximal position.

The device of FIG. 10A can for example be of a length of 96 mm, although other lengths are contemplated. Note that in this embodiment, the length from the beads 118, 120 to the tail is relatively small. Thus, it has a shorter frame and a shorter membrane. In the embodiment of FIGS. 11A-11F, the device 110' is identical to device 110 of FIG. 10A except it has a longer length in the collapsed position (and expanded position) from the beads 118', 120' to the tail. The length of the distal collar position is the same in device 110' as in device 110 and the length of the proximal collar position is the same in device 110' as device 110'. The length of device 110' can be the same overall length as device 110. Since in all other respects, device 110' is the same as device 110, the identical components/features have been designated with "prime" reference numerals, e.g., adjustable collar 115', tail portion 112', frame 116' beads 118', 120', membrane 122', etc.

Note that although two positions are shown, it is also contemplated that the collar can have more than two positions to provide more than two expanded positions of the wire and membrane to provide more than two sizes in the single device.

It should be appreciated that the adjustable collar of FIG. 10A can be provided on any of the devices described herein to adjust the size of the device.

The devices disclosed herein are not made of copper or a reactive material and thus do not act like a drug. They are designed to fill the uterine cavity and provide increased surface area. They are preferably flexible to better fill the cavity. The beads do not necessarily need to be configured or positioned to block the fallopian tubes.

A delivery system for the herein described intrauterine devices of the present invention is shown in FIGS. 14-16D. The delivery system includes an outer delivery tube 160 and an inner delivery tube 170 slidable received in the lumen 161 of the outer tube 160. Outer tube 160, as shown in FIGS. 16A-16C includes a collar or stop 162 to limit proximal and/or distal movement via contact with the patient's body. The outer tube can have a tapered distal portion 163.

Inner tube 170, as shown in FIGS. 15A-15C has slot (or slit) 172 at a distal end dimensioned to receive the tail portion of the intrauterine device. The device is positioned in the elongated slot 172 such that the tail is retained by the inner tube 170 and the frame and membrane of the device extend distally of the distal edge 174 of the inner tube 170. When the outer tube 160 overlies the slot 172 of the inner tube 170, the tail portion is retained: when the outer tube 160 is retracted relative to the inner tube 170 (or the inner tube 170 is advanced relative to the outer tube or both the inner tube 170 advanced and the outer tube 160 retracted), the tail portion is exposed for release of the intrauterine device into the uterine cavity. A sample packaging for the intrauterine device and delivery system is shown in FIG. 17 which has a lower tray 180 and upper lid 182. The packaging can also include a uterine sound 189 used to examine the vaginal cavity and measure the depth of the uterus. The intrauterine device can be packaged adjacent but non-engaged with the slot of the inner tube. Alternatively, the device could be packaged with the tail portion positioned in the slot, i.e., preloaded. If packaged as shown in FIG. 17, the device is in the placement (unconstrained) position. The intrauterine device shown in FIG. 17 is device 120 of FIG. 12A, however, the other uterine devices disclosed herein could alternatively be packaged and used with the delivery system.

In use, the tail 122 of the uterine device 120 is initially placed within the slot 172 in the inner tube 170 (if not packaged within the slot). The inner tube 170 is pulled back within the outer tube 160 to collapse the frame 126 and membrane 132 for delivery into the uterine cavity. This position is shown in FIG. 18A wherein the frame 120 is within the outer tube 160 with only the beads 128, 130 exposed. Once inserted in the uterine cavity, relative movement of the inner tube 170 and outer tube 160, e.g., pulling the outer tube 160 back or moving the inner tube 170 forward, exposes the slot 172 and tail portion 122 and enables self-expansion of the frame 126 and membrane 132 to release the device from the delivery system as shown in FIGS. 18A and 18C wherein the device 120 is partially deployed as it is exposed and then fully deployed for release as in FIG. 18D.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. An intrauterine device for preventing egg fertilization comprising:
    a) a membrane;
    b) a frame having a first arm and a second arm, the first and second arms movable from a first position to a second more expanded position, wherein the first and second arms each have a curve extending outwardly, the frame supporting the membrane to move the membrane between a first position to a second more expanded position, wherein the first and second arms are non-planar and each arm has a proximal portion, an intermediate portion and a distal portion, the first arm has a first bend at the intermediate portion so the intermediate portion of the first arm lies in a different plane than the proximal portion of the first arm and the second arm has a second bend at the intermediate portion so the intermediate portion of the second arm lies in a different plane than the proximal portion of the second arm, the membrane at an intermediate region curving inwardly toward a distal region due to the first and second bends; and
    c) an elongated tail portion positioned proximal of the membrane.

2. The device of claim 1, wherein the membrane has a proximal portion closer to the tail portion and a distal portion, the distal portion having a convex end.

3. The device of claim 2, wherein the convex end spans a width of the membrane from the first arm to the second arm.

4. The device of claim 1, wherein the frame is V-shaped.

5. The device of claim 1, wherein the first arm terminates in a first bead and the second arm terminates in a second bead, and the first and second beads are radiopaque.

6. The device of claim 5, wherein the frame and first and second beads have a silicone coating thereover.

7. The device of claim 1, wherein the frame has a silicone coating thereover.

8. The device of claim 1, wherein the membrane is composed of a non-copper material.

9. The device of claim 1, wherein the membrane is composed of a non-reactive material.

10. The device of claim 1, wherein the membrane lies in multiple planes.

11. The device of claim 1, wherein the membrane extends between the first and second arms of the frame to provide a top cover, side covers and bottom cover.

12. The device of claim 1 in combination with a delivery system, the delivery system having an inner tube with an elongated slot to receive the tail portion and an outer tube, the inner tube positioned within the outer tube, the outer tube maintaining the frame in the first position.

13. The device of claim 12, wherein the outer tube and inner tube are relatively movable.

14. An intrauterine device for preventing egg fertilization comprising:
    a) a membrane;
    b) an elongated tail portion positioned proximal of the membrane; and
    c) a frame having a first arm and a second arm, the first and second arms movable from a first position to a second more expanded position, the frame supporting the membrane to move the membrane between a first position to a second more expanded position, wherein the first and second arms each have a proximal portion, an intermediate portion and a distal portion, the membrane supported between the first and second arms and having a proximal portion closer to the tail portion and a distal portion, the distal portion having a convex end formed along a distalmost edge of the membrane extending across the membrane from a left side to a right side, the first arm terminating in a first bead and the second arm terminating in a second bead, the distalmost edge terminating proximal of the first and second beads.

15. The device of claim 14, wherein the membrane has an intermediate region extending inwardly with respect to a distal region.

16. The device of claim 14, wherein the frame and first and second beads have a silicone coating thereover and the first and second beads are radiopaque.

17. The device of claim 14, wherein the convex end spans a width of the membrane from the first arm to the second arm, and the membrane extends between the arms of the frame to provide a top cover, side covers and bottom cover.

18. The device of claim 14, wherein the membrane is composed of a non-copper material.

19. The device of claim 14, wherein the membrane is composed of a non-reactive material.

20. The device of claim 14, in combination with a delivery system, the delivery system having an inner tube with an elongated slot to receive the tail portion and an outer tube, the inner tube positioned within the outer tube, the outer tube maintaining the frame in the first position and the outer tube and inner tube are relatively movable.

* * * * *